US009682345B2

(12) United States Patent
Gromala et al.

(10) Patent No.: US 9,682,345 B2
(45) Date of Patent: Jun. 20, 2017

(54) METHOD OF TREATING A CLEANROOM ENCLOSURE

(71) Applicants: Particle Measuring Systems, Inc., Boulder, CO (US); Particle Measuring Systems, S.R.L., Fonte Nuova (Rome) (IT)

(72) Inventors: Gerald Gromala, Broomfield, CO (US); Ronald W. Adkins, Monkton, MD (US); Gilberto Dalmaso, Fonte Nuova (IT); Brian A. Knollenberg, Windsor, CO (US); Daniel Rodier, Louisville, CO (US)

(73) Assignees: PARTICLE MEASURING SYSTEMS, INC., Boulder, CO (US); PARTICLE MEASURING SYSTEMS, S.R.L., Rome (IT)

( * ) Notice: Subject to any disclaimer, the term of this patent is extended or adjusted under 35 U.S.C. 154(b) by 0 days.

(21) Appl. No.: 14/793,500

(22) Filed: Jul. 7, 2015

(65) Prior Publication Data
US 2016/0008757 A1    Jan. 14, 2016

Related U.S. Application Data

(60) Provisional application No. 62/021,842, filed on Jul. 8, 2014, provisional application No. 62/107,979, filed on Jan. 26, 2015.

(51) Int. Cl.
| B01D 53/82 | (2006.01) |
| A61L 9/12 | (2006.01) |
| B01D 53/44 | (2006.01) |
| B01D 53/46 | (2006.01) |
| A61L 2/00 | (2006.01) |
| A61L 9/00 | (2006.01) |
| B01D 53/32 | (2006.01) |
| B01D 53/72 | (2006.01) |

(52) U.S. Cl.
CPC ............... *B01D 53/82* (2013.01); *A61L 2/00* (2013.01); *A61L 9/00* (2013.01); *A61L 9/12* (2013.01); *B01D 53/323* (2013.01); *B01D 53/44* (2013.01); *B01D 53/46* (2013.01); *B01D 53/72* (2013.01); *B01D 2251/104* (2013.01); *B01D 2257/708* (2013.01); *B01D 2257/91* (2013.01); *B01D 2258/06* (2013.01); *B01D 2259/4508* (2013.01)

(58) Field of Classification Search
CPC ... B01D 53/82; A61L 2/00; A61L 9/00; A61L 9/12
USPC ........................................................ 588/300
See application file for complete search history.

(56) References Cited

U.S. PATENT DOCUMENTS

| 4,049,400 | A | 9/1977 | Bennett et al. |
| 5,474,600 | A | 12/1995 | Volodina et al. |
| 5,492,677 | A | 2/1996 | Yoshikawa |
| 5,549,735 | A | 8/1996 | Coppom |
| 5,593,476 | A | 1/1997 | Coppom |
| 6,033,301 | A | 3/2000 | Suwa |
| 6,352,579 | B1 | 3/2002 | Hirata et al. |
| 6,364,935 | B1 | 4/2002 | Wennerstrom |
| 6,497,754 | B2 | 12/2002 | Joannou |
| 6,508,982 | B1 | 1/2003 | Shoji |
| 6,620,385 | B2 | 9/2003 | Fujii |
| 6,805,732 | B1 | 10/2004 | Billiotte et al. |
| 6,849,100 | B2 | 2/2005 | Lim et al. |
| 7,025,806 | B2 | 4/2006 | Coppom et al. |
| 7,156,898 | B2 | 1/2007 | Jaisinghani |
| 7,198,660 | B2 | 4/2007 | Billiotte et al. |
| 7,279,028 | B2 | 10/2007 | Bergeron et al. |
| 7,384,456 | B2 | 6/2008 | Aubert |
| 7,407,633 | B2 | 8/2008 | Potember et al. |
| 7,449,053 | B2 | 11/2008 | Hallam |
| 7,452,410 | B2 | 11/2008 | Bergeron et al. |
| 7,452,411 | B2 | 11/2008 | Volodina et al. |
| 7,513,933 | B2 | 4/2009 | Coppom et al. |
| 7,531,141 | B2 | 5/2009 | Descotes et al. |
| 7,582,144 | B2 | 9/2009 | Krigmont |
| 7,695,690 | B2 | 4/2010 | Taylor et al. |
| 7,771,672 | B2 | 8/2010 | Bergeron et al. |
| 7,815,719 | B2 | 10/2010 | McKinney et al. |
| 7,815,720 | B2 | 10/2010 | McKinney |
| 7,931,859 | B2 | 4/2011 | Mlodzinski et al. |
| 8,003,058 | B2 | 8/2011 | Bergeron et al. |
| 8,012,248 | B2 | 9/2011 | Yun |

(Continued)

FOREIGN PATENT DOCUMENTS

| EP | 0 627 263 | 12/1994 |
| EP | 1 562 646 | 4/2006 |

(Continued)

OTHER PUBLICATIONS

International Search Report with Written Opinion corresponding to International Patent Application No. PCT/US2015/039403, mailed Sep. 30, 2015.

*Primary Examiner* — Edward Johnson
(74) *Attorney, Agent, or Firm* — Lathrop & Gage LLP

(57) ABSTRACT

This invention is in the field of systems and methods for controlling contamination in high purity environments. This invention relates generally to particulate filtering and treatment of molecular contamination and process gases in enclosures, such as cleanrooms, contamination controlled manufacturing environments, mini-environments, isolators, glove boxes and restricted air barrier systems (RABS). The invention is capable of chemically transforming molecular contamination and process gases into less reactive or inert reaction products while at the same time decreasing the level of biological and nonbiological particulates.

23 Claims, 9 Drawing Sheets

(56) References Cited

U.S. PATENT DOCUMENTS

| | | |
|---|---|---|
| 8,123,840 B2 | 2/2012 | Marra |
| 8,211,374 B2 | 7/2012 | Hallam |
| 8,663,362 B2 | 3/2014 | Hagan |
| 2005/0115213 A1 | 6/2005 | Lim et al. |
| 2006/0185511 A1 | 8/2006 | Tepper |
| 2007/0263338 A1 | 11/2007 | Nakashima et al. |
| 2008/0063577 A1 | 3/2008 | Crowe et al. |
| 2009/0120047 A1 | 5/2009 | Perrier et al. |
| 2013/0025462 A1 | 1/2013 | Yun |

FOREIGN PATENT DOCUMENTS

| | | |
|---|---|---|
| EP | 1 638 666 | 6/2010 |
| WO | WO 95/07759 | 3/1995 |

METHOD OF TREATING A CLEANROOM ENCLOSURE

CROSS-REFERENCE TO RELATED APPLICATIONS

This application claims the benefit of priority to U.S. Provisional Patent Application Nos. 62/021,842 filed Jul. 8, 2014 and 62/107,979 filed Jan. 26, 2015, each of which is hereby incorporated by reference in its entirety.

BACKGROUND

The manufacture of many classes of products requires precisely controlled chemical environments characterized by stringent criteria on the acceptable levels of particulate and/or gas phase contaminants. Semiconductor and microelectronics processing, for example, requires very low levels of molecular and particulate contaminants to provide high purity materials and processing conditions enabling a wide range of state of the art products. Similarly, the manufacture of pharmaceutical and biological products requires highly sterile environments characterized by low levels of biologically active contaminants to address safety and efficacy considerations.

Currently, the electronic manufacturing industry relies primarily on filtration for removal of particulate to maintain cleanroom conditions. Filtration is typically achieved by pumping ambient gas through either a high efficiency particulate air (HEPA) or an ultra-low penetration air (ULPA) filtration system. HEPA and ULPA filtration are capable of achieving low particulate levels but require a substantial pressure drop to transport gas through the dense filters necessary for effective particulate collection. Additionally, current HEPA and ULPA filtration systems remove almost no airborne molecular contamination (AMC), such as volatile organic compounds (VOCs). The VOCs can lead to surface molecular contaminations, such as residues, within the electronics, which may substantially impact physical, chemical, electrical, or optical performance. As a result, it is necessary for some semiconductor and microprocessing applications to implement chemical filtration to effectively reduce the concentration of AMC, which introduces additional cost, pressure drop and uncertainty regarding filter performance over time.

The pharmaceutical industry also must ensure that chemical composition of manufacturing and handling environments are precisely controlled. Currently, aseptic environments for the manufacture of pharmaceutical and biological products are typically achieved by a combination of filtration and sterilization processes. Filtration, as in the electronic manufacturing industry, relies on HEPA or ULPA filtration systems. Sterilization is typically achieved by treating the enclosure with one or more gas-phase sterilants, such as vaporized hydrogen peroxide (VHP), formaldehyde or chlorine dioxide. Filtration is continuous and compatible with typical operation conditions of the enclosure, whereas sterilization requires the enclosure to cease operation while the gas-phase sterilant is present.

The highest current standard for aseptic pharmaceutical manufacturing is Grade A and ISO Class 5 which requires a particulate contamination level below 3520 particulates per cubic meter at 0.5 µm and less than 1 colony forming unit (CFU) per cubic meter. Particulate contamination is typically continuously monitored during production using suitable instrumentation, such as an optical particle counter. Biological contamination is typically monitored using growth-based culture methods requiring samples to be taken using settling plates or impactors provided within the enclosure over specified time intervals and subsequently monitored for bacterial growth. Under standard culture protocols, bacterial growth may not appear for 24 hours or longer after exposure, thus requiring any pharmaceutical made or tested within the enclosure to be stored while bacteria is allowed to grow and environmental monitoring data reviewed before the product is released for shipment. If sufficient bacteria are identified in culture, pharmaceutical products corresponding to a relevant time period may need to be destroyed and the enclosure decontaminated.

While HEPA filtration combined with gas sterilization is capable of meeting Grade A and ISO Class 5 standards these techniques are susceptible to certain practical issues limiting the ability to efficiently control and maintain aseptic conditions. First, conventional HEPA filtration methods are unable to remove some viruses having small physical dimensions (e.g., <0.2 µm) and conventional methods for sterility assurance, such as growth-based culture methods, do not effectively detect some viruses that require living cells to replicate. Accordingly, reliance on HEPA filtering alone may raise the potential for viral contamination that is difficult to assess using conventional sterility assurance methods. Second, trapped microbial contaminants within HEPA filters can develop into a biofilm, thereby compromising the sterility of filter processing. For example, some biofilm are extended, microbial colonies which eventually enter a dispersion phase in which individual cells break free and seek to replicate on other surfaces potentially contaminating an aseptic environment between sterilizations. Third, there is a risk that trapped microorganisms that are difficult to detect may become liberated from a HEPA filter over time. For example, some individual bacterial spores do not form colonies while in a weakened state but are considered viable but non-culturable. In addition, some vegetative bacterial or fungal cells will not form colonies on standard agar growth-culture media and, thus, will also go undetected via sterilization assurance monitoring. These problems present significant risks of undetected contamination and therefore, cleanroom management commonly employs frequent decontamination using gas-phase sterilants to ensure sterile conditions.

Gas-phase sterilants are very effective at deactivating biological contaminants. However, a drawback of using a gas-phase sterilant is that the after an enclosure is treated (the decontamination phase) the enclosure must be aerated for a period of time to reduce the concentration the gas-phase sterilant (the aeration phase) to a human exposure limit. After sterilization with VHP, for example, enclosures are typically aerated for 4-5 hours in order to reduce the concentration of VHP to the human exposure limit of 1 part per million. Moreover, new protocols for VHP decontamination for certain applications require aeration to continue until a 10 part per billion concentration of VHP is reached, thus requiring 8-9 hours. As the enclosure cannot be used for production during the aeration phase, such aseptic processes directly impact overall throughput and productivity. Thus, managing enclosure sterility presents a practical tradeoff as to the extent and frequency of aseptic decontamination cycles which impact throughput and the risk of contamination and associated costly destruction of potentially contaminated products.

As will be understood from the foregoing, there remains a need in the art for processing systems and methods capable of achieving efficient filtration and processing of cleanroom enclosures. For example, processing systems and methods are needed for cleanroom and manufacturing applications that provide effective inactivation and removal of biological particles or for the degradation of process gases, such as sterilants, or molecular contaminants, such as VOCs. In addition, aseptic processing systems are needed for cleanroom and manufacturing applications that decrease the frequency and non-productive time required for process gas and gas-phase sterilant decontamination processing, for example, by decreasing the time an enclosure cannot be used due to the presence of process gas or gas-phase sterilant present, for example, during aeration phase.

SUMMARY

This invention provides systems and methods for gas processing and treatment of enclosures, such as cleanroom enclosures. This invention relates generally to particulate filtering and treatment of molecular contamination and process gases in enclosures, such as cleanrooms, contamination controlled manufacturing environments, equipment front end modules, mini-environments, isolators, glove boxes, freeze dryers and restricted air barrier systems (RABS). The invention is capable of chemically transforming molecular contaminants or process gases into less reactive or inert reaction products while at the same time decreasing the level of biological and nonbiological particulates.

Provided herein are active filtration systems and methods related to treatment of enclosures, such as cleanrooms for manufacturing applications ranging from semiconductor materials and microelectronic systems to pharmaceutical and biological products. Embodiments of the invention provide an active filtration system which combines a filtration system for removing particles with a process(es) capable of inactivation of biological particles and/or degradation of molecular contaminants, particulate contaminants and/or process gases. Further, certain embodiments of the invention are capable of effectively filtering, and optionally inactivating, airborne particles, either biological or non-biological, out of gas in an enclosure via electrostatic filtering of particulate by cycling gas through an active filtration system in fluid communication with the enclosure, for example, provided in a closed loop configuration. Further, certain embodiments of the invention are capable of efficient tandem removal of particles and degradation of process gases and/or molecular or particulate contaminants using a pressure drop less than that provided using conventional HEPA and ULPA filtering techniques.

In an aspect, the invention provides a method for treating a cleanroom enclosure comprising the steps of: (i) providing the cleanroom enclosure; and (ii) flowing gas from within the cleanroom enclosure through an active filtration system or flowing gas through the active filtration system into the cleanroom enclosure, wherein the active filtration system decomposes one or more of molecular contaminants, particulate contaminants and/or process gases present in the gas into reaction products and reduces the abundance of particles present in the gas. In certain embodiments, the method of treating achieves a degradation of one or more process gases, such as a gas phase sterilant(s), within a cleanroom enclosure or within gas transported into or out of a cleanroom enclosure. In certain embodiments, the method of treating achieves a degradation of molecular and/or particulate contaminants, within a cleanroom enclosure or within gas transported into or out of a cleanroom enclosure. In certain embodiments, the method of treating achieves a reduction of particulates, for example via removal by filtering, within a cleanroom enclosure or within gas transported into or out of a cleanroom enclosure and, thus are capable of implementation with a lower energy consumption footprint that conventional cleanroom treatment methods.

Methods and systems of the present invention are versatile and, thus, are compatible with a range of enclosure environments and applications. In some embodiments, for example, the enclosure comprises a cleanroom, an equipment front end module, a mini-environment, a contamination controlled manufacturing environment, a glove box, a restricted air barrier system, an isolator or a freeze dryer. In an embodiment the enclosure is located within a cleanroom and/or is a component of a clean room system. In embodiments, the reaction products are less reactive then the molecular contaminants, particulate contaminants, and optionally for some embodiments the reaction products are inert reaction products.

In some embodiments, for example, the gas is a process gas within the cleanroom enclosure or an exhaust gas removed from the cleanroom enclosure. In some embodiments, for example, the gas is air or process gas from outside of the enclosure. In some embodiments, for example, the method further comprises a step of monitoring a flow rate of the gas into or out of the enclosure or monitoring a flow rate of the gas through the active filtration system. In some embodiments, for example, the method further comprises a step of monitoring a particle concentration within the enclosure or within the active filtration system. In some embodiments, for example, the method further comprises a step of monitoring a residence time of the gas within the enclosure or within the active filtration system.

In an aspect, the active filtration system comprises a corona discharge, for example, comprising a low power, alternating current corona discharge. In some embodiments, the active filtration system generates ozone, for example using a current corona discharge, such a concentration of ozone selected from the range 1 part per billion to 3 parts per million, or, for example, less than 10 parts per million. In an embodiment, the active filtration system comprises a HEPA filter, a ULPA filter and/or an electrostatic filter. In embodiments, the active air filtration system does not include either a HEPA filter or an ULPA filter, for example, to avoid the significant pressure drop associated with these types of filters. In an embodiment, for example, the method further comprises a step of monitoring the ozone concentration within the enclosure.

In an aspect, the methods and systems of the invention further include sensing of one or more characteristics of the enclosure, gas and/or active filtration system, and optionally control of treatment steps and/or conditions on the basis of such sensing, including closed loop feedback control. In embodiments, for example, the method further comprises the steps of: (i) monitoring at least one first parameter of the enclosure or the active filtration system; and (ii) adjusting at least one second parameter of the active filtration system in a controlled feedback loop based on the monitoring of the first parameter to control the decomposition of molecular contaminants, process gases or any combination thereof or to control the reduction of particles. In an embodiment, the first parameter is selected from the group comprising: an ozone concentration, a microbial contaminant concentration, a particulate concentration, an electrostatic charge, a pressure, a gas flow rate, a gas velocity, and a concentration of airborne molecular contamination (AMC); and the second parameter is selected from the group comprising: an ozone concentration, a pressure, an electrostatic charge, a gas flow rate and a gas velocity.

An important aspect of the methods and systems of the invention is use of an active filtration system to reduce the amount (e.g., number, concentration, number density, etc.) of particles in the enclosure, gas provided to the enclosure, gas removed from the enclosure or any combination of these. The present systems and methods are compatible with a range of filtering approaches and components. In an embodiment, for example, the electrostatic filter comprises an electrostatic precipitator, for example, wherein particles are charged and electrostatic biasing us used to enhance collection, capture and/or removal. In an embodiment, the electrostatic filter comprises a HEPA or ULPA filter component, for example, alone or in combination with an electrostatic precipitator. In certain embodiments, the active filtration system reduces the particles in the gas to a level characteristic of a Grade A and ISO class 5 particulate environment or better. Advantageously, in some embodiments the active filtration system exhibits a pressure drop of less than or equal to 30 Pa, optionally for some embodiments, the active filtration system exhibits a pressure drop selected from the range of 5 Pa and 30 Pa.

The active filtration system and methods can be used advantageously in the manufacture of electronics. The systems and methods are capable of decomposing volatile organic compounds and refractory compounds used in the manufacture of electronics into inert reaction products, representing a significant improvement over current filtration technology without the addition secondary purifiers or expensive disposal of process gases which are to be remediated.

In an aspect, the enclosure is a contamination controlled enclosure for the production of electronic systems or optical systems. In an embodiment, for example, the active filtration system and methods are applied to an enclosure for the preparation, manufacture, transport, processing or storage of electronics, for example, semiconductors, optical materials, microelectronic systems, data storage devices, LED devices flat panel displays or similar devices. In an embodiment, the enclosure is located within a semiconductor manufacturing facility. In embodiments, one or more process gases are intentionally introduced during a manufacturing process step.

In embodiments, the process gases and/or molecular contaminants comprise process gases for semiconductor and/or microelectronics systems such as volatile organic compounds and refractory compounds. In certain embodiments, the molecular contaminants or process gases comprise one or more of isopropanol, acetone, diethylamine, triethylamine, cyclosiloxanes, hexamethyldisilizane, phthalates, toluene, xylene, benzene, benzaldehyde, benzoic acid, ethylbenzene, methyl isobutyl ketone, phenol, acetophenone, hexanol, butylated hydroxytoluene, dimethylamino (trimethyl)silane, 1-methoxy-2-propyl acetate (PGMEA), triethyl phosphate, 1-methyl-2-pyrrolidinone (NMP), cyclohexanone and decane. In embodiments, the reaction products comprise one or more compounds that can be effective eliminated from the enclosure, for example via pumping, flushing, filtering and/or evacuation techniques, without negatively impacting processing conditions, for example by avoiding generation of residue in the enclosure. In an embodiment, for example, the reaction products comprise one or more of $H_2O$, $CO_2$, $CO$, $O_2$, $N_2$, $NO_x$, $SO_x$, and $CH_4$. In certain embodiments, for example, the active filtration system reduces the concentration of one or more volatile organic compounds or refractory compounds present in the one or process gases by at least 90%, or optionally, for some examples, by at least 95% or by at least 99%.

Methods and systems of the invention are versatile and effective at decontamination of an enclosure during aseptic processing and maintaining sterile conditions during operation of the enclosure, for example, for the preparation, manufacture, and packaging of pharmaceutical and/or biological products. For example, embodiments of the present invention enhance the efficiency of conventional aseptic processing by reducing the amount of aeration time required after the introduction of a gas-phase sterilant to an enclosure by passing gas from the enclosure through an active filtration system to efficiently decompose the gas-phase sterilants into reaction products, such as nontoxic and/or inert reaction products, including water, oxygen and nitrogen. In addition, systems and methods of certain embodiments are also capable of inactivating and removing biological contaminants, including microbes, viruses, and fungi, and thus are compatible with establishing and maintaining sterile conditions by cycling gas in an enclosure through an active filtration system.

In some embodiments, the methods of the present invention further include the steps of passing gas in the enclosure through the active filtration system to inactivate and remove biological particles and returning treated gas back to the enclosure, for example, to maintain sterile conditions during use of the enclosure for manufacture of sterile products such as pharmaceutical and/or biological products and/or during aeration for reducing the concentration of gas-phase sterilants. In certain embodiments, the enclosure is used in for preparation, manufacture, storage, transfer, fill or finish of a sterile pharmaceutical or biological, a sterile pharmaceutical or biological container, or sterile pharmaceutical or biological delivery device. Optionally, in some embodiments the enclosure is for preparation, manufacture, storage, transfer, or processing of food or drink. Optionally, in some embodiments the enclosure is for the preparation, manufacture, storage, transfer or processing of a cosmetic. In certain embodiments, the active filtration system reduces the viability of biological particles or contaminants in the gas.

The systems and methods of the system are versatile and support both enhanced efficiency of aseptic processing and effective maintenance of aseptic conditions during use of the enclosure, for example, during manufacture or packaging of pharmaceutical and biological products. In some embodiments, the system and methods further comprise introducing a gas-phase sterilant into the enclosure for a sufficient time to effect sterilization of the gas and surfaces, wherein after sterilization the active filtration system is used to decompose the gas-phase sterilant into reaction products. In some embodiments, for example, sterilizing gas and surfaces within the enclosure by introducing the gas-phase sterilant occurs during a conditioning phase and a decantamination phase and reducing the concentration of the gas-phase sterilant in the enclosure occurs during an aeration phase. In embodiments, for example, the gas flowing into the active filtration system is air from outside of the enclosure. In certain embodiments, reducing concentration of the gas-phase sterilant in the enclosure occurs by transporting the gas through an active filtration system and out of the enclosure. In certain embodiments, reducing the concentration of the gas-phase sterilant in the enclosure occurs by transporting the gas through the active filtration system and returning treated gas to the enclosure. The invention includes methods further comprising the step of circulating gas from the enclosure through the active filtration system and back to the enclosure, for example in a closed loop fluid configuration, during an aeration phase and/or operation phase to inactivate and remove biological particles, thereby effectively maintaining aseptic conditions.

In certain embodiments, the active filtration system reduces the viability of biological particles, for example bacteria, bacterial spores, fungi, fungal spores, viruses or molds in the gas. Optionally, some embodiments further comprise a step of monitoring microbial contaminant level within the enclosure. Some embodiments further comprise the step of monitoring a least one of concentration of particulate contamination, concentration of molecular contamination, ozone concentration, electrostatic charge, pressure, or gas flow rate.

In some embodiments, the active filtration system generates ozone, for example using a current corona discharge, at a concentration sufficient to cause efficient decomposition of gas-phase sterilant such as gas-phase $H_2O_2$, for example, during an aeration phase of an aseptic process. In certain embodiments, the active filtration system generates ozone within the active filtration system having a concentration less than 10 parts per million so as to avoid exposure of the enclosure to levels of ozone that can cause harm to products and/or personnel within the enclosure. In certain embodiments, the method further comprises a step of monitoring a concentration of ozone in the enclosure.

An additional advantage of some embodiments of the present systems and methods is that the active filtration system is capable of efficiently decomposing gas-phase sterilants, for example by transporting gas from the enclosure through the active filtration system, and optionally returning treated gas to the enclosure having a reduced level of gas-phase sterilant. Sterilant decomposition is beneficial because it reduces the amount of time required to aerate an enclosure after a gas-phase sterilant has been introduced, thereby allowing the enclosure to be used more frequently and productively. In an embodiment, for example, sterilant decomposition is achieved by reaction with $O_3$ generated by the active filtration system, for example, to generate water and oxygen decomposition products. Alternatively, decomposition of sterilants is achieved via reaction with radicals, ions and/or electrons generated by the active filtration system. Alternatively, decomposition of sterilants is achieved via exposure to electromagnetic radiation, for example have wavelengths in the UV or visible regions of the electromagnetic spectrum, generated by the active filtration system. Optionally for some embodiments, the reaction products from the decomposition of gas-phase sterilant are $H_2O$, $CO_2$, $O_2$, $N_2$ or any combination of these. Further, in some embodiments the reducing step reduces the concentration of a gas-phase sterilant(s) in the enclosure to below 1 part per million over a time period of less than 3 hours. In some embodiments, the gas-phase sterilant comprises one or more of hydrogen peroxide, ethylene oxide, or formaldehyde. In a specific embodiment, for example, the gas-phase sterilant comprises $H_2O_2$ and the reaction products comprise oxygen and water. In another embodiment, for example, the gas-phase sterilant comprises ethylene oxide and the reaction products comprise one or more of $H_2O$, CO2, and $O_2$.

In an embodiment, for example, the method further comprises reducing humidity within the enclosure prior to the step of sterilizing gas and surfaces within the enclosure by introducing the gas-phase sterilant into the enclosure. In embodiments, for example, the sterilizing step further comprises increasing the concentration of the gas-phase sterilant in the enclosure. Optionally for some embodiments, the sterilizing step comprises maintaining a concentration of the gas-phase sterilant within the enclosure for a sufficient time to effect sterilization of the gas and surfaces. In some embodiments, for example, the concentration of the gas-phase sterilant in the enclosure is increased to and maintained at a concentration selected from the range of 0.1-10 mg/L. In some embodiments, for example, the concentration of the gas-phase sterilant is maintained for a duration selected from the range of 20 minutes to 180 minutes. Optionally, in certain embodiment, the method further comprises a step of monitoring the concentration of gas-phase sterilant in the enclosure or, optionally, monitoring pressure, gas flow rate, gas velocity, temperature, humidity or any combination of these within the enclosure. In certain embodiments, a temperature within the enclosure is maintained at a value selected from the range of 10-60 degrees Celsius during the sterilizing step. In embodiments, the method does not generate a residue in the enclosure.

The methods contained herein may be used in conjunction with aseptic processing of a variety of enclosures, particularly enclosures for the manufacture of pharmaceutical products, biological products and other sensitive materials. In certain embodiments, the enclosure and the active filtration system comprise a closed system.

The methods and systems of the invention are effective for inactivation and removal of a variety of biological particles. A benefit of the active filtration system is that it functions to decontaminate and maintain sterile conditions and, thus, may reduce the frequency of sterilization of an enclosure via aseptic processing. In some embodiments both the active filtration system and the gas-phase sterilant are used to inactivate biological particles. In one embodiment for example, the biological particles comprise one or more of a bacterium, a bacterial spore, a fungus, a fungal spore, a virus, and a mold. In an embodiment, the method further comprises a step of monitoring the microbial contaminant level within the enclosure. Optionally, in an embodiment, the method of the invention does not generate a residue in the enclosure, for example, by only generating gas-phase reaction products from the decomposition of gas-phase sterilants.

In an aspect, the invention provides a method of reducing the concentration of sterilant process gas(es) in a cleanroom enclosure after a decontamination phase comprising the steps of: (i) providing the cleanroom enclosure containing the sterilant process gas; and (ii) flowing gas from within the cleanroom enclosure through an active filtration system, wherein the active filtration system decomposes the sterilant process gases present in the gas to reaction products, inactivates biological particles present in the gas and filters particles present in the gas. In an embodiment, for example, the method further comprises returning gas treated by the active filtration system to the cleanroom enclosure or exhausting the gas treated by the active filtration system to outside of the cleanroom enclosure. In an embodiment, the method of this aspect further comprises any of the additional process steps and/or process conditions described herein.

In an aspect, the invention provides a method for controlling aseptic conditions within a cleanroom enclosure comprising the steps of: (i) providing aseptic conditions in the cleanroom enclosure; (ii) flowing gas from within the cleanroom enclosure through an active filtration system, wherein the active filtration system decomposes a gas-phase sterilant present in the gas into reaction products, inactivates biological particles present in the gas and filters airborne particles present in the gas; and (iii) flowing the gas treated by the active filtration system from an outlet into the enclosure or outside of the enclosure. In an embodiment, for example, the step of providing the aseptic conditions comprises sterilizing gas and surfaces within the enclosure by introducing a gas-phase sterilant into the enclosure for a sufficient time to effect sterilization of the gas and surfaces. In an embodiment, comprises exhausting the gas treated by the active filtration system to outside of the cleanroom enclosure. In an embodiment, the method of this aspect further comprises any of the additional process steps and/or process conditions described herein.

In an aspect, the invention provides a method for controlling the gas composition within a cleanroom enclosure for the manufacture of electronics or optical systems comprising the steps of: (i) providing the enclosure for the manufacture of electronics or optical systems; and (ii) flowing gas from within the cleanroom enclosure through an active filtration system or flowing gas through an active filtration system into the cleanroom enclosure, wherein the active filtration system decomposes one or more volatile organic compounds or refractory compounds present in the gas to reaction products and filters particles present in the gas. In an embodiment, for example, the one or more process gases are transformed to reactions products that are more easily eliminated from the enclosure than that the process gases, for example, compounds that do not result in formation of residues in the enclosure. In an embodiment, for example, the one or more process gases are transformed to reactions products that are less toxic than the process gases and/or reaction products that are more chemically inert than the process gases. In an embodiment, for example, the method further comprises exhausting the gas treated by the active filtration system to outside of the cleanroom enclosure. In an embodiment, the method of this aspect further comprises any of the additional process steps and/or process conditions described herein.

In an aspect, the invention provides a system for controlling conditions in a cleanroom enclosure comprising: an active filtration system in fluid communication with the cleanroom enclosure for reducing a concentration of one or more molecular contaminants or process gases in the cleanroom enclosure, wherein the active filtration system receives gas from the cleanroom enclosure or provides gas to the cleanroom enclosure, decomposes the one or more molecular contaminants or process gases to reaction products and reduces the abundance of particles present in the enclosure. In an embodiment, the system of this aspect is for carrying out any of the methods described herein. In an embodiment, for example, the one or more molecular contaminants is one or more volatile organic compounds or refractory compounds. In an embodiment, for example, the one or more process gases is one or more gas-phase sterilants.

In an embodiment, for example, a gas inlet of the active filtration system is provided in fluid communication with the enclosure. In an embodiment, the system further comprises a fluid actuator for transporting the gas from the enclosure through the active filtration system and/or returning treated gas to the enclosure and/or transporting gas through the active filtration system into the enclosure or outside the enclosure. In certain embodiments, the fluid actuator is a pump or a fan. In some embodiments, for example, wherein the fluid actuator transports the gas through the active filtration system and away from the enclosure. In an embodiment, the fluid actuator transports the gas through the active filtration system and returns treated gas to the enclosure. In certain embodiments, a gas outlet of the active filtration system is positioned in fluid communication with the enclosure. In certain embodiments for example, the enclosure and the active filtration system comprise a closed system, for example wherein gas is transported from the enclosure through the active filtration system and treated gas having reduced levels of viable biological particles and/or gas-phase sterilants are returned to the enclosure.

In certain embodiments, the enclosure comprises a cleanroom, an equipment front end module, mini-environment, a contamination controlled manufacturing environment, a glove box, a restricted air barrier system, an isolator or a freeze dryer. In certain embodiments, the enclosure is located within a cleanroom. In some embodiments, for example, the enclosure is for preparation, manufacture, storage, transfer, fill or finish of a sterile pharmaceutical or biological product, a sterile container for a pharmaceutical or biological product or a sterile delivery device a pharmaceutical or biological product. In embodiments, for example, the enclosure is for preparation, manufacture, storage, transfer or processing of food or drink. In certain embodiments, the enclosure is for preparation, manufacture, storage, transfer or processing of a semiconductors, optical materials, microelectronic systems, data storage devices, LED devices, or flat panel displays. In certain embodiments, the enclosure is for preparation, manufacture, storage, transfer or processing of a cosmetic.

DETAILED DESCRIPTION

Figure 1:
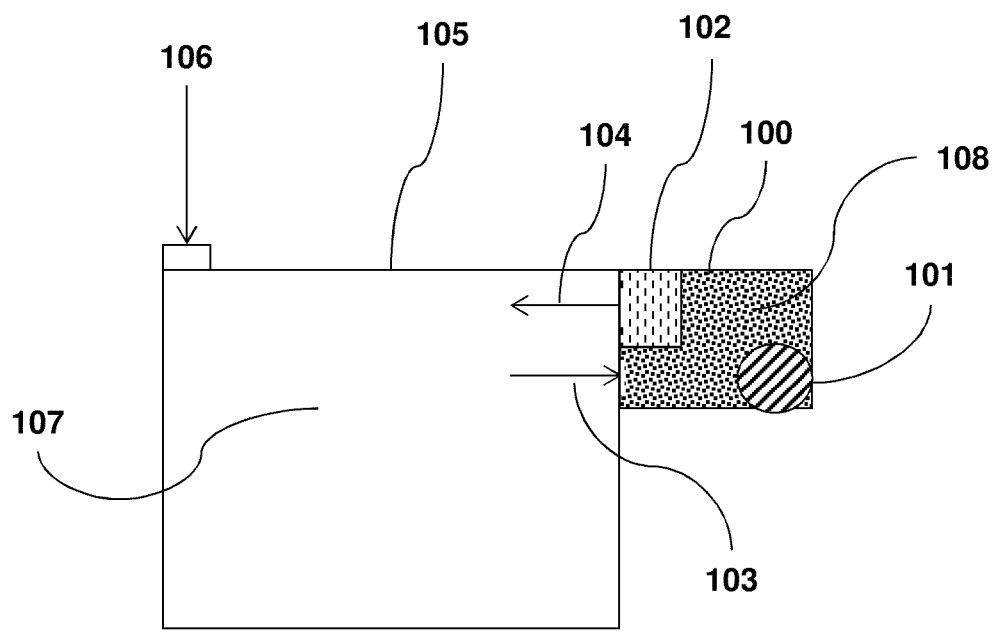
FIG. 1 provides a schematic diagram depicting an enclosure and active filtration system in standard operation.

In general the terms and phrases used herein have their art-recognized meaning, which can be found by reference to standard texts, journal references and contexts known to those skilled in the art. The following definitions are provided to clarify their specific use in the context of the invention.

"Enclosure" refers to any enclosed space, for example, an enclosed space capable of excluding, inactivating or removing particulates and/or biological contaminants from ambient gases. Enclosures may include but are not limited to, cleanrooms, isolators, glove boxes and restricted air barrier systems. Enclosures may be part of either a closed or open system. Enclosures may contain gas comprising breathable air and/or other gases or mixtures of gases, including process gases that do not contain oxygen.

"Treating" refers to the process of filtering, decontaminating, sterilizing, removing, degrading and/or otherwise manipulating material within a space in order to achieve a desired controlled environment, for example, a controlled composition environment characterized by specific limits on the concentration of contaminants, such as particulate contaminants, biological particle contaminants and/or molecular contaminants. For example, treating may include but is not limited to manipulating material within a gas by removing particles, decreasing the viability of microbial contaminants, and/or decomposing molecular contaminants or process gases.

"Gas-phase sterilant" refers to one or more gas-phase species used to inactivate biological contaminants including but not limited to: vaporized hydrogen peroxide (VHP), other peroxides, ozone, formaldehyde, chlorine dioxide and ethylene oxide. Gas-phase sterilant includes liquid sterilants heated to achieve volatility to the gas-phase, such as VHP. Vaporized Hydrogen Peroxide (VHP) is generally accepted as preferred gas-phase sterilant due to its formation of water and oxygen as non-toxic and stable decomposition products.

"Active filtration system" refers to a gas-phase filtration system that performs more than one filtration, gas phase decomposition and/or sterilization functions. Often, one function will be physical filtration while the second will be a chemical, electrical and/or optical decomposition function, such as decomposition of one or more process gases. In an embodiment, for example, an active filtration system combines a filter component that performs physical filtration of particulate using a mesh or electrostatic filter while also treating a gas stream with reactive species and/or electromagnetic radiation, such as ozone, free radicals, ions, electrons and/or ultraviolet radiation. Active filtration systems are useful for treating a range of gases including air and process gases, such as process gases for manufacturing processes, maintaining cleanroom conditions and/or aseptic processing.

"Conditioning phase" refers to a period in an aseptic process in which gas-phase sterilant is added in order to increase the concentration of gas-phase sterilant to a specified level. The conditioning phase begins at the introduction of the gas-phase sterilant and ends when the concentration has reached the desired level for the decontamination phase.

"Decontamination phase" refers to a period in an aseptic process in which the gas-phase sterilant has reached sufficient concentration within an enclosure to inactivate some biological contaminants and gas-phase sterilant concentration is no longer substantially being increased.

"Aeration phase" refers to a period in an aseptic process in which the concentration of gas-phase sterilant is decreasing from the concentration reached during the decontamination phase but the concentration remains above the human exposure limit for the specific gas-phase sterilant being used. Typically, the aeration phase includes the removal, decomposition and/or dilution of gas-phase sterilant.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may refer to nonbiological particle and biological particles, such as viruses, spores and microorganisms including bacteria, fungi, archaea, protists, and other single cell microorganisms. Biological particles include, but are not limited to, microorganisms having a size on the order of 0.1-20 µm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 50 nm, 100 nm, 1 µm or greater, or 10 µm or greater. Specific particles include particles having a size selected from 50 nm to 50 µm, a size selected from 100 nm to 10 µm, or a size selected from 500 nm to 5 µm.

"Biological contaminant" refers to biological particulates, including viable biological particles capable of reproduction. Biological contaminant includes but is not limited to: microorganisms, microbes, bacteria, fungi, archaea, protists, viruses, and prions.

"Electrostatic filter" or "electrostatic precipitator" refers to a filtration device that removes small particulates by generating an electrostatic field on a collector, such as a grid, mesh or impactor, which attracts and removes particulates with relatively low impedance to the overall gas flow through the filter. Electrostatic filters may include a component for charging particles prior to removal.

"Treated gas" refers to gas that has been passed through an active air filter to inactivate and/or remove particles and/or reduce the concentration of process gases, such as gas-phase sterilants and volatile organic compounds.

"Inert reaction products" refer to chemical species which would require activation energy to react at room temperature and atmospheric pressure including but not limited to: water, carbon dioxide, oxygen, and nitrogen.

"Fluid communication" refers to the configuration of two or more components such that a fluid (e.g., a gas or a liquid) is capable of transport, flowing and/or diffusing from one component to another component. Elements may be in fluid communication via one or more additional elements such as tubes, containment structures, channels, valves, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

"Aseptic manufacturing" refers to describe a method of production for sterile pharmaceuticals including parenteral drugs, ophthalmic solutions, Active Pharmaceutical Ingredients (API), and Active Biological Ingredients (API) to name a few.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum or volume exerting zero force per unit area. Absolute pressure is distinguished from a "differential pressure" or "gauge pressure", which refers to a relative or difference in force exhibited per unit area in excess of or relative to a second pressure, such as an ambient pressure or atmospheric pressure.

"Contamination controlled manufacturing environment" refers to an enclosure in which the composition within the enclosure is actively controlled. For example, an enclosure may have air as the ambient gas while minimizing contaminant gas such as VOCs, refractory compounds, gas-phase sterilants and other toxic gases. Alternatively, the ambient gas may be a one or more process gases where the environment is controlled to maintain a prespecified concentration.

"Volatile organic compound (VOC)" refers to an organic compound (i.e. a compound containing carbon) that exhibits some vapor pressure at room temperature and atmospheric pressure and, thus, has a propensity to evaporate to some degree even at low temperatures and pressures. VOCs are typically not acutely toxic but have been linked to a number of adverse health effects in humans such as eye, nose and throat irritation; headaches; loss of coordination; nausea; and damage to the liver, kidneys, and central nervous system. Many VOCs are also considered to be carcinogenic. As such acceptable VOC levels and emissions are often regulated by government agencies such as the EPA and OSHA. As used herein, VOC refers to any organic compound capable of vaporization and is not limited to those expressly referenced by regulatory agencies. Some non-limiting examples of VOCs are benzene, methylene chloride, isopropyl alcohol (isopropanol), formaldehyde, "Refractory compound" broadly refers to organic compounds that contain atoms other than C, H, N, and O. The most problematic refractory compounds are those that contain Si atoms. For example, trimethylsilanol, hexamethyldisiloxane, hexamethyldisilazane, and cyclosiloxanes such as D4, D5, D6, etc. Examples of other compounds that would be considered refractory that do not contain Si atoms include triethylphosphate and tetrachloroethylene.

Systems and Methods for Aseptic Processing

FIG. 1 provides a schematic diagram depicting an active filtration system 100 during standard operation of a sterilization system, in which cleanroom conditions are present within the enclosure 105. In this embodiment, the active filtration system 100 is comprised of a low-concentration ozone generator 101 producing reactive gases, such as hydroxyl radicals, oxygen radicals or ozone, 108 within the filtration system and an electrostatic filter 102. The enclosure 105 contains a gas 107 under cleanroom conditions such as a controlled level of airborne particulates and biological particles. Gas flows through a filter inlet valve 103 into the active filtration system 100 where it is sterilized by the reactive gas 108 and filtered through the electrostatic filter 102. Gas is then returned from the active filtration system 100 to the enclosure 105 via a filter outlet valve 104. In an embodiment both the filter inlet valve 103 and filter outlet valve 104 remain open and gas continuously flows through the active filtration system 100 or the filter inlet valve 103 and filter outlet valve 104 may be open and closed to intermittently flow gas through the active filtration system 100. The gas-phase sterilant valve 106 remains closed.

Figure 2:
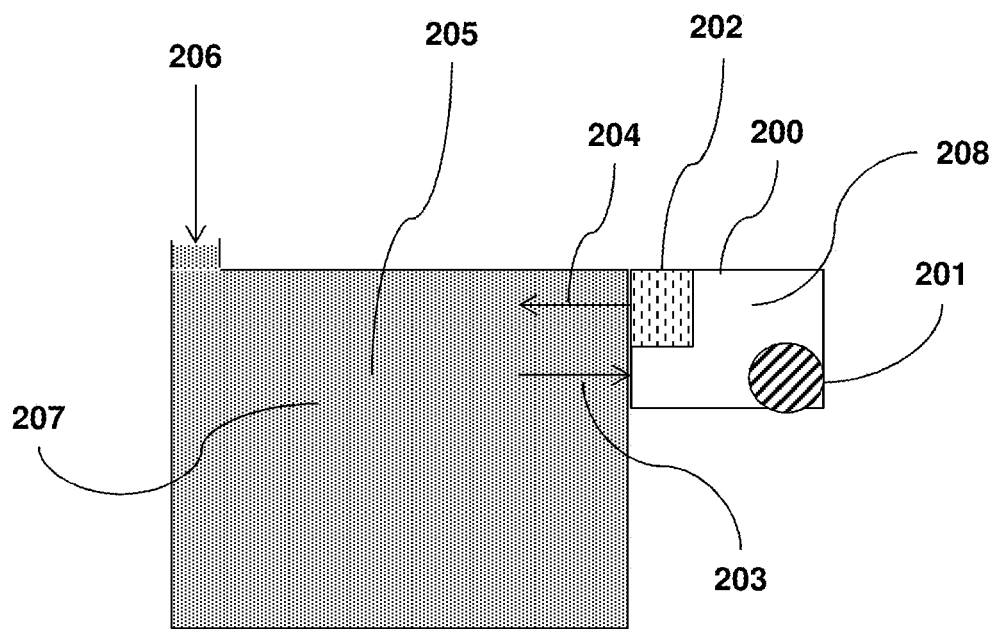
FIG. 2 provides a schematic diagram depicting an enclosure and active filtration system during the conditioning phase.

FIG. 2 provides a schematic diagram depicting an active filtration system 200 during the conditioning phase of the decontamination process. The enclosure 205 is manipulated to specific environmental conditions for decontamination, such as temperature, pressure, and/or humidity. The gas-phase sterilant valve 206 is opened and a gas-phase sterilant 207 is introduced into the enclosure 205, mixing with the ambient gas. Both the filter inlet valve 203 and filter outlet valve 204 are closed to prevent the gas-phase sterilant from entering the active filtration system 200. The ozone generator 201 and electrostatic filter may be either left operating or powered off. The gas 208 within the active filtration system 200 may be low-concentration ozone, residual ozone, hydroxyl radicals, oxygen radicals or ambient gas.

Figure 3:
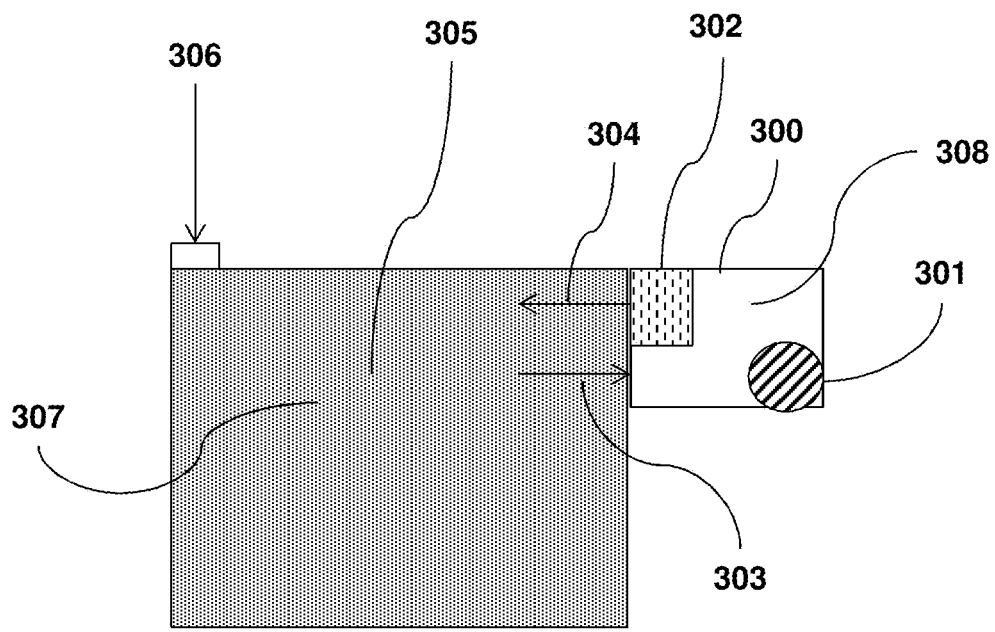
FIG. 3 provides a schematic diagram depicting an enclosure and active filtration system during the decontamination phase FIG. 4 provides a schematic diagram depicting an enclosure and active filtration system during the aeration phase.

FIG. 3 provides a schematic diagram depicting an active filtration system 300 during the decontamination phase of the decontamination process. Once the concentration of gas-phase sterilant 307 has reached a sufficiently high concentration within the enclosure 305, the gas-phase sterilant valve 306 is closed. In some embodiments the concentration will be maintained for a set period of times to increase the effectiveness of decontamination. Both the filter inlet valve 303 and filter outlet valve 304 remain closed to prevent the gas-phase sterilant from entering the active filtration system 300. The ozone generator 301 and electrostatic filter may be either left operating or powered off. The gas 308 within the active filtration system 300 may be low-concentration ozone, residual ozone, hydroxyl radicals, oxygen radicals or ambient gas.

Figure 4:
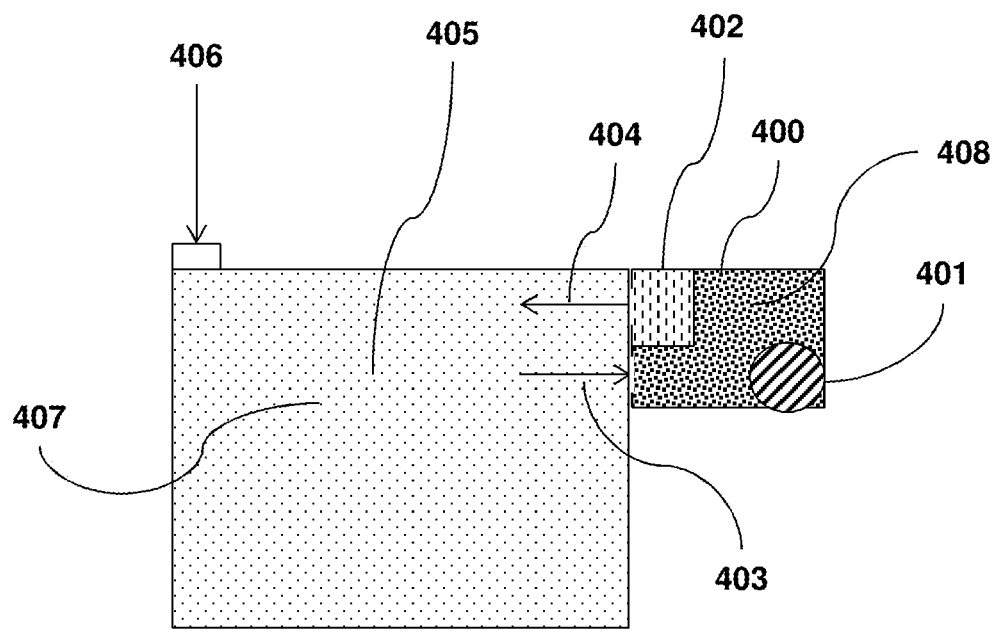

FIG. 4 provides a schematic diagram depicting an active filtration system 400 during the aeration phase of the decontamination process. After the decontamination phase is complete gas-phase sterilant in the enclosure 405 must be removed before the returning to standard operation. Optionally, the enclosure 405 may be vented and/or ambient gas pumped into the enclosure 405 through the gas-sterilization inlet 406 or some other inlet to help lower the concentration gas-phase sterilant within. Both the filter inlet valve 403 and filter outlet valve 404 are opened to allow gas-phase sterilant to begin to flow through the active filtration system 400. The active component of the active filtration system 408, in one embodiment ozone, begins to react with the gas-phase sterilant, reducing sterilant concentration and creating reaction products. The sterilant may also be decomposed through exposure to an air plasma. The gas is then passed through the electrostatic filter 402 to remove particulates and treated gas is returned to the enclosure 405. The aeration phase continues until the concentration of gas-phase sterilant 407 reaches operating conditions, for example the human exposure limit.

Figure 5:
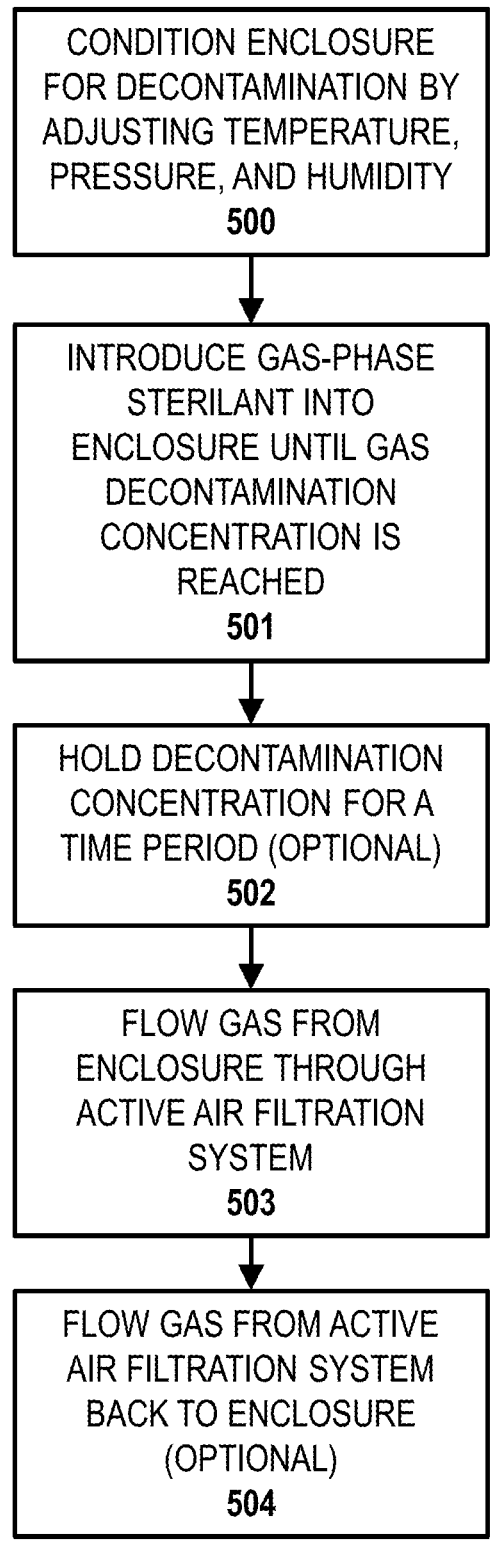
FIG. 5 provides a flow diagram illustrating a method for sterilization of an enclosure using an active filtration system.

FIG. 5 provides a flow diagram illustrating a method of decomposing a gas-phase sterilant using an active filtration system. In the first step 500, the enclosure is prepared for sterilization using a gas-phase sterilant by adjusting physical parameters, for example temperature, pressure and water vapor concentration, to preselected conditions that favor sterilization. In the decontamination phase 501, a gas-phase sterilant such as vaporized hydrogen peroxide is added to the enclosure until a preselected sterilization concentration sufficient to decontaminate biologically active contaminants is reached. After the preselected concentration is reached, an optional step 502 is to maintain the decontamination concentration for a preselected time in order to further ensure sterilization. In the aeration phase 503, the ambient gas containing gas-phase sterilant is pumped through the active filtration system which reacts with the gas-phase sterilant to create reaction products, such as gaseous oxygen and water vapor, and decreases the concentration of gas-phase sterilant. In some embodiments the ambient gas is pumped through the active filtration system back into the enclosure 504.

Systems and Methods for Manufacture of Microelectronics

In the manufacture of microelectronics, some of the most damaging types of AMCs are compounds which are not readily removed by conventional adsorption/reaction type chemical filtration. These are typically compounds which are not strongly reactive and have high vapor pressures under normal operating conditions. A few examples include isopropanol (IPA) and trimethylsilanol (TMS). Trimethylsilanol frequently exists in semiconductor manufacturing facilities as decomposition by product of hexamethyldisilazane (HMDS). HMDS is used in wafer processing to promote film adhesion to the wafer surface. When it becomes airborne it reacts with water to create ammonia and TMS. TMS is very difficult to trap with conventional chemical filters due to its high vapor pressure and lack of reactivity. When TMS migrates through filters into photolithography tools, it can become photo-oxidized, generating molecular silicon dioxide which can irreversibly deposit on the surface of precision optical components.

In an active filtration system, a compound such as TMS is decomposed into silicon dioxide, water, and carbon dioxide, for example, through reactions with free electrons, hydroxyl radicals and oxygen radicals. The silicon dioxide is easily removed by a conventional fiber filter and the water and carbon dioxide are harmless to the manufacturing processes.

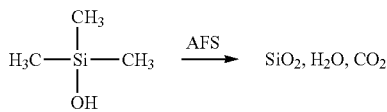

IPA is also difficult to remove air by conventional adsorption chemical filtration as it has a high vapor pressure. In a similar manner, active filtration systems can decompose IPA into harmless water and carbon dioxide.

Figure 6:
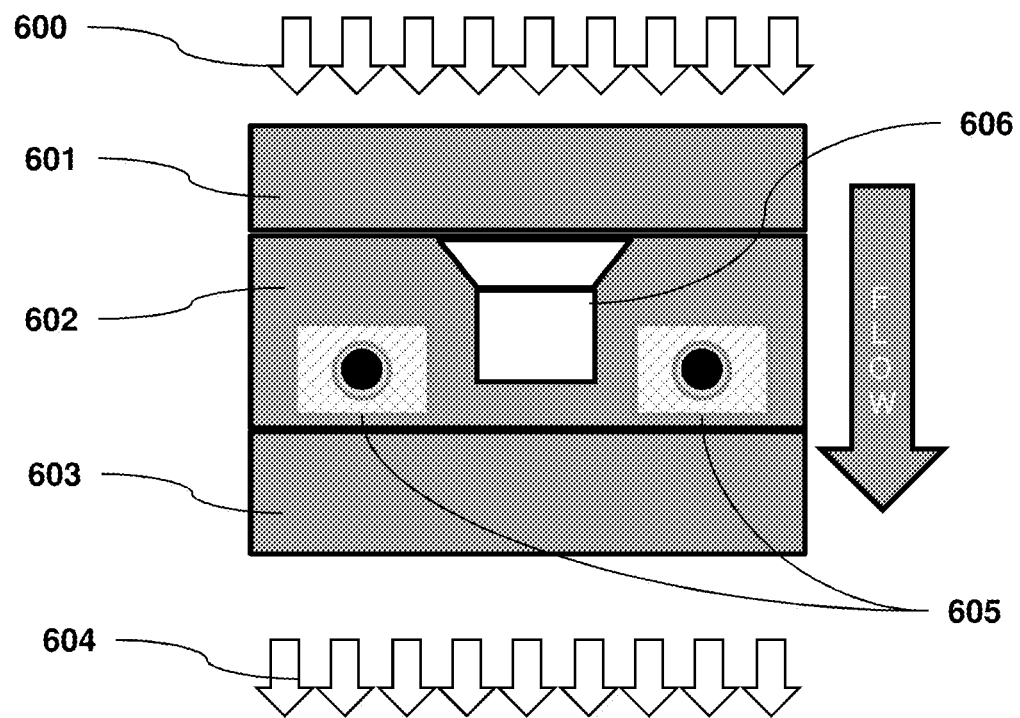
FIG. 6 provides a schematic diagram illustrating a method for controlling contamination and cleanroom conditions using an active air filtration system.

FIG. 6 provides a schematic diagram illustrating a method and system for decomposing volatile organic compounds and refractory compounds using an active filtration system. As shown in this Figure, untreated gas from a cleanroom enclosure containing VOCs or refractory compounds 600 is forced through an active air filtration system via a fluid actuator 606, such as a pump or fan. The arrows provided in FIG. 6 show the direction of the gas flow. Within the active filtration system two corona discharge sources 605 provide electromagnetic radiation, free electrons, ions and/or radicals, such as hydroxyl radicals, oxygen (singlet and triplet) radicals, and/or ozone in a mixing chamber 602. Interaction of the output of the corona discharge sources and the gas decomposes VOCs and refractory compounds, thereby generating reaction products that can be effectively collected and removed from the gas, such as less reactive or inert reaction products. Optionally, in some embodiments a molecular absorption filter 601 filters the gas before it enters the mixing chamber 602. After the gas has interacted with the sources 605, it then passes through an electrostatic filter 603 which removes particulate contaminants. In some embodiments the electrostatic filter 603 is combined with, or alternatively replaced by, a fiber or membrane filter such as a HEPA or ULPA filter, for example, for the purpose of filtration of carbon containing reaction products from the active filtration system. Clean gas 604 is then recirculated by return from the outlet of the active filtration system to the cleanroom enclosure or transported out of the system as exhaust.

Figure 7:
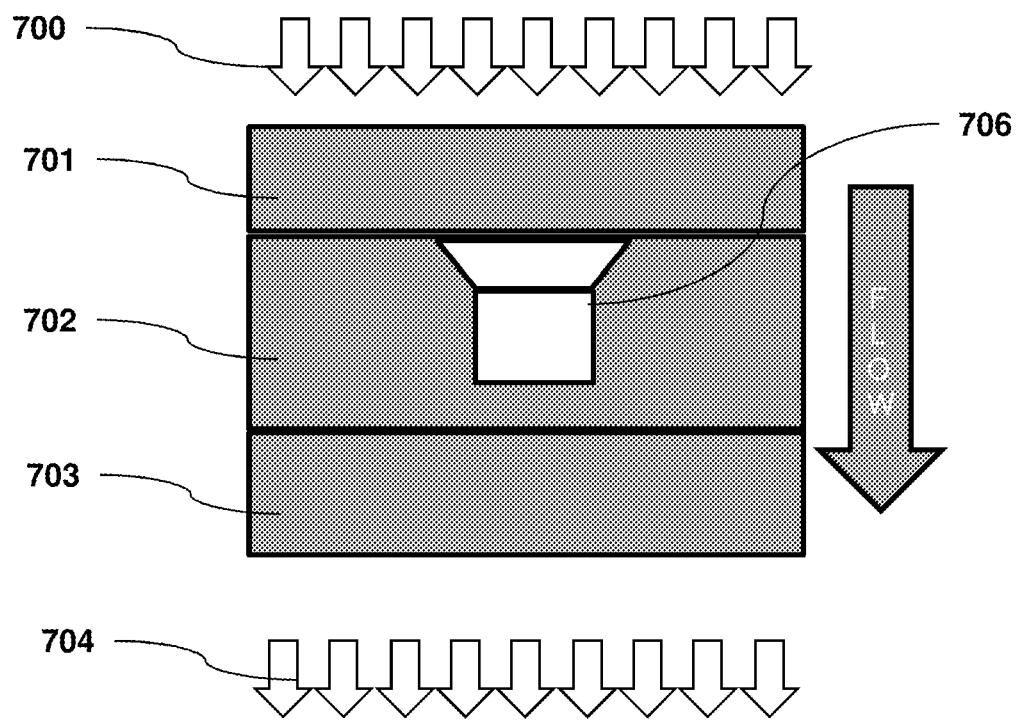
FIG. 7 provides a flow diagram illustrating the current method of controlling contamination and cleanroom conditions.

For comparison, FIG. 7 provides a schematic diagram illustrating a conventional system and method of treating gas for a cleanroom enclosure that does not include use of an active air filtration system. As shown in this Figure, untreated gas 700 is pumped through a molecular absorption filter 701 into a mixing chamber 702 by an actuator 706. The gas is then pumped through a fiber or membrane filter 703. Molecular contaminants or process gases present in the mixing chamber, however, are not effectively removed by the fiber or membrane filter 703. Treated gas 704 then flows into the cleanroom enclosure or out of the system as exhaust, therefore, potentially still containing VOCs or refractory compounds.

Figure 8:
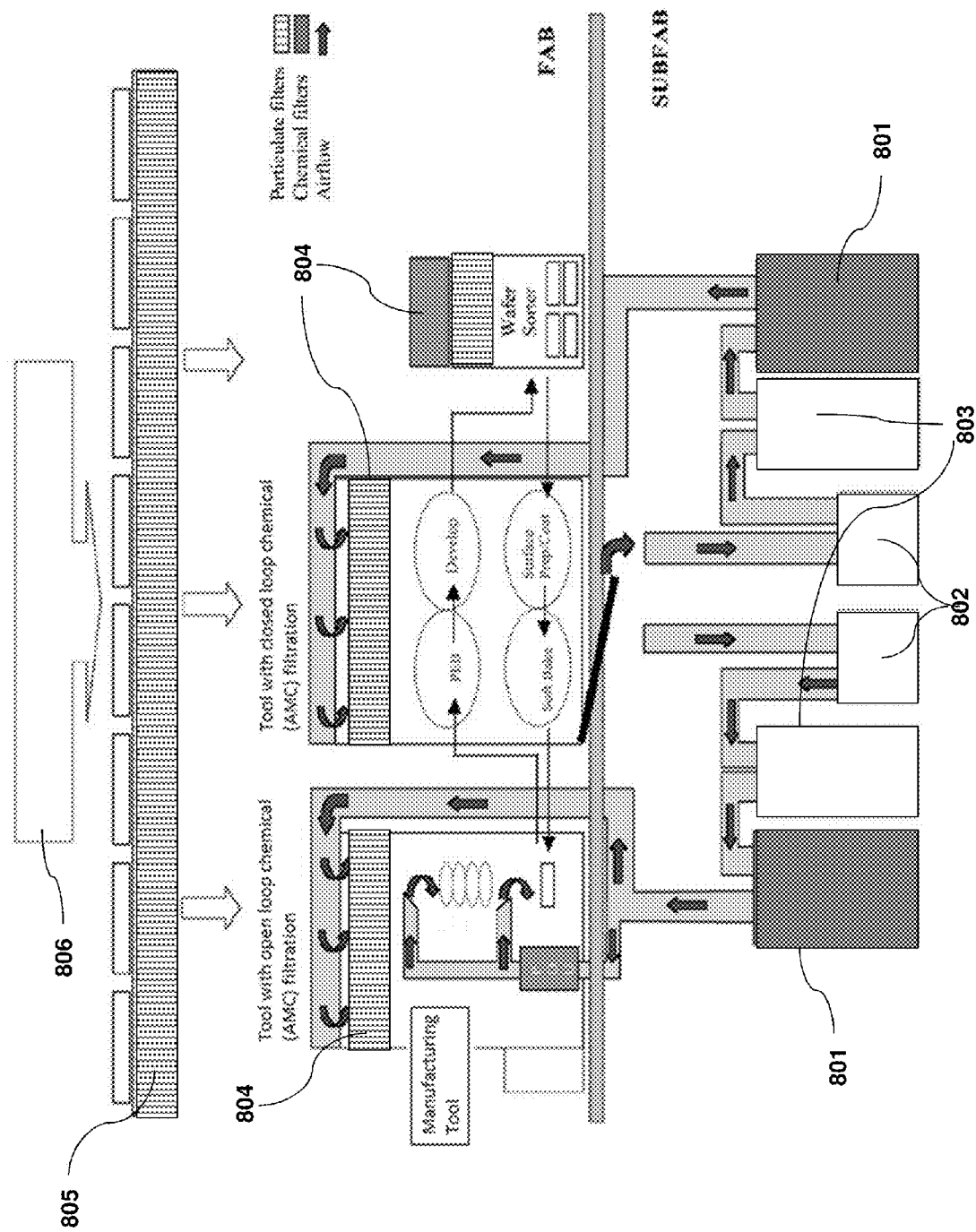
FIG. 8 provides an example of a microelectronics facility cleanroom enclosure filtration system including an active filtration system.

FIG. 8 provides a schematic illustration of an active filtration system as part of a comprehensive air handling system in an electronics production facility. Make up and recirculated air 806 flows through a ceiling grid of particulate filters 805, such as one or more HEPA filters. Gas from the cleanroom enclosures flows through a blower 802 into an environmental control unit 803 which regulates physical parameters such as pressure, flow rate, humidity and temperature. The gas is then pumped into the active filtration system 801 which treats the gas, for example by decomposing molecular contaminants, particular contaminants and/or process gases and by reducing the abundance of particles. The gas is then returned to the enclosure, for example, via transport through a secondary ULPA filter 804.

Figure 9:
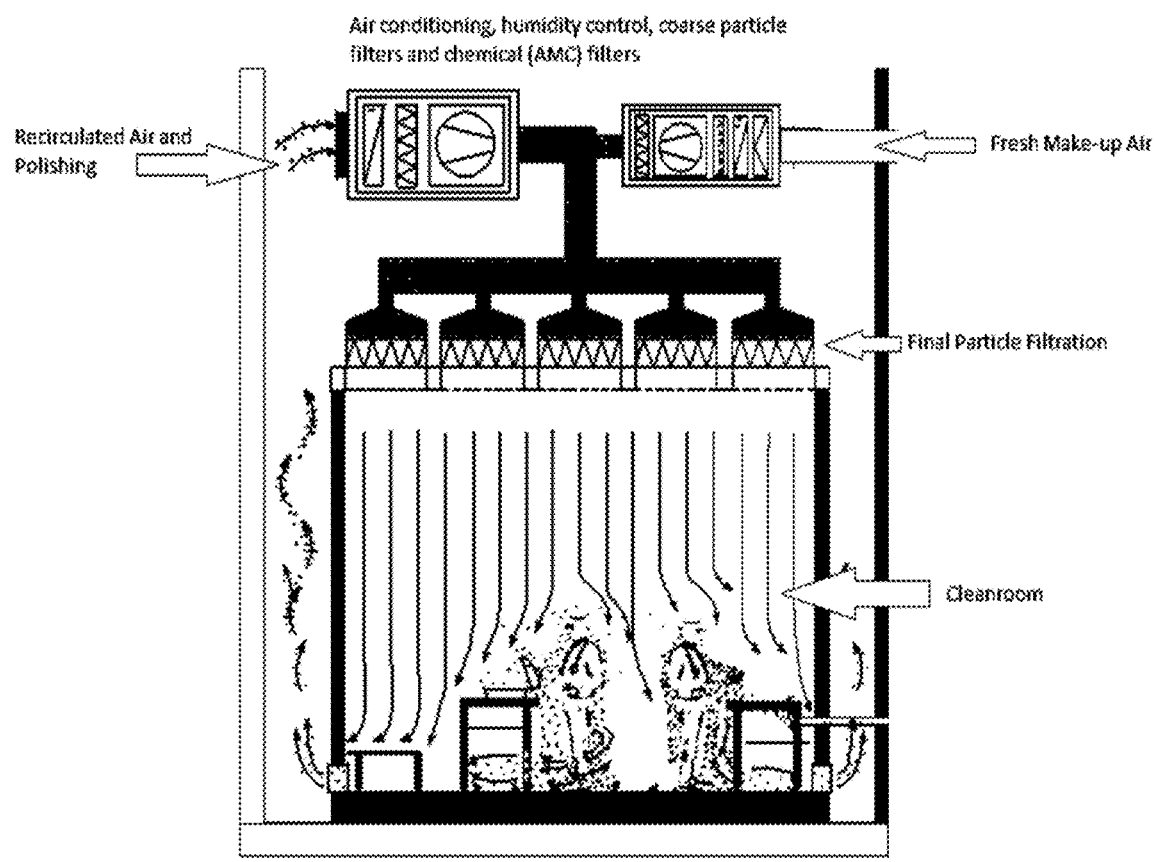
FIG. 9 provides a schematic diagram illustrating a conventional cleanroom air handling system.

FIG. 9 provides a profile view of a cleanroom filtration loop. Recirculated gas from within the cleanroom (left) or fresh make-up gas from outside of the clean room (right) is forced through a filtration system. The initial filtration system includes air conditioning, humidity controls, coarse particle filters, chemical filter and, optionally, an active filtration system. The gas is then forced through a final particle filter before it enters the cleanroom enclosure. Gas continually flows from the cleanroom enclosure back through the filtration system to remove molecular or particulate contaminants within the cleanroom.

The invention may be further understood by the following non-limiting examples.

Example 1: Active Filtration System for Aseptic Processing

The active filtration system in this example supplements or replaces the use of traditional High Efficiency Particulate Air (HEPA) or Ultra-Low Penetration Air (ULPA) filters used to control particulate and microbial contamination in aseptic drug production. An example of an active filtration system useful for the embodiments described in this example is the AirManager active air filtration and sterilization system developed by Quest International Ltd and distributed by AAR Corp., and as described in U.S. Pat. Nos. 7,449,053 and 8,211,374, or an equivalent thereof. The active filtration system filters both particulate and microbial contaminations which are two primary requirements of an aseptic environment that can affect the drug product quality and ultimately patient safety. Additionally, the invention provides a new benefit in controlling aseptic conditions by reducing the time needed to decontaminate the drug production equipment and machinery (for example production and sterility assurance isolators) where VHP is used as the sterilizing agent. It should be noted that there are several other environmental parameters that are controlled during aseptic production including pressure, air flow velocity, temperature and relative humidity.

The active filtration system consists of an electrostatic filter media and a low-power ozone generator packaged together in an enclosure that contains the ozone field so the gas exiting the filter is at a physiologically acceptable level without the use of an ozone decomposition catalyzer. During drug production, the active filtration system electrostatic filter is capable of maintaining ISO Class 5 particulate levels in a single pass by charging particulates as they pass through the low-power ozone generator enabling collection and retention, for example, using a collector and applied electric field. Further, the active filtration system maintains aseptic drug production conditions by eradicating microbial organisms which pass through the filter providing a log-12 reduction in viruses and a log-5 reduction in bacteria and fungi. The active filtration system only requires a 10 Pa pressure drop at new operating conditions, as opposed to the 100 Pa pressure drop associated with standard, new HEPA filters. The 10 times reduction in pressure drop corresponds to a 5 times to 10 times reduction in the energy requirement of HVAC fans responsible for maintaining air flow through the filter.

Decontamination Process

Decontamination of the enclosure using VHP may still be required, although less frequently. The decontamination process consists of four phases: (1) Dehumidifying; (2) Conditioning; (3) Sterilization; and (4) Aeration.

In the Dehumidifying phase, the relative humidity is decreased to between 10-30% and the temperature of the enclosure is increased. The reduction in humidity allows for a rapid increase in VHP concentration during the Conditioning phase, decreasing the total decontamination time.

In the Conditioning phase, the active filtration system is removed from fluid communication with the enclosure and a vaporized 31% $H_2O_2$ solution is pumped into the enclosure using a generator such as the Steris® VHP 1000. Additional VHP is added until a predetermined concentration (typically greater than 0.5 mg/L) is achieved within the enclosure. Once the predetermined concentration is reached, VHP supply to the enclosure can be modulated to maintain a constant concentration and the Sterilization phase begins.

In the Sterilization phase, the VHP concentration is maintained for a predetermined time. The time of the Sterilization phase is affected by the predetermined concentration of VHP, as higher concentration will require less time to inactivate any residual biological contaminants. The active filtration system remains removed from fluid communication to the enclosure during the sterilization phase.

In the Aeration phase, the active filtration system is activated and put into fluid communication with the enclosure. As the VHP gas is pumped through the active filtration system, the ozone contained within the active filtration system oxidizes the flowing VHP into water and gaseous oxygen. Due to the ozone-VHP reaction, the concentration of VHP decreases to the human exposure limit of 1 ppm in significantly less time than using a conventional enclosure without an active filtration system. Without an active filtration system the aeration phase typically takes 4-5 hours to reach a concentration 1 ppm or 8-9 hours to reach a concentration of 10 ppb. Use of the active filtration system reduces the aeration time required by at least 10%, optionally for some applications at least 30% and optionally for some applications at least 50%. The active filtration system also removes particulates that may have been introduced during the decontamination of the enclosure, ensuring that at the end of the aeration phase the enclosure is fully ready for production.

Problems Addressed

HEPA filters are the current standard used in aseptic manufacturing to provide the required levels of particulate and microbial removal. This approach may satisfy the requirement for an ISO Class 5 particulate environment. The case is not nearly as definitive for microbial contamination however. There are four examples of this. The first is that these trapped microbes develop into a biofilm over time. The biofilm is a complex, extended colony that is capable of sustaining itself for prolonged periods of time with the final stage in its lifecycle called dispersion. At the point of dispersion, individual cells comprising the outer layer of the film break free and seek to relocate to a new surface and start the biofilm process anew. What may comprises a significant risk factor, however, is if the rogue cells are liberated from the filter media and follow the air flow (0.45 m/sec typically) and breach the aseptic air space during a manufacturing operation.

Related to the case of biofilm dispersion, the second example is the risk factor associated with bacterial spores if they become liberated from the HEPA filter over time. This occurrence is similar to the biofilm risk in the sense that contamination of the sterile production environment is completely random and can pose regulatory compliance problems for as long as the offending filter is in service. Bacterial spores do not always form colonies when collected on the growth media for a variety of reasons largely having to do a physical weakened state the spore is in. This phenomenon is known as Viable but Non-Culturable (VBNC). This presents an obvious risk because microbial contamination could have been present during a drug product production run but went undetected because the traditional growth-based method used in sterility assurance did not produce a colony.

The third example demonstrating a third risk factor involving traditional HEPA filtration relates to vegetative bacterial or fungal cells being present but going undetected (do not form colonies on the growth media) using the standard cGMP collection method based on impaction because of physical damage caused during the sampling process (VBNC state).

Perhaps the most compelling and fourth risk factor associated with traditional HEPA filters relates to viruses in aseptic drug production. The current sterility assurance regulations specify the use of growth-based culture methods to monitor for the presence of microbial contamination during manufacturing or QA activities. It is common knowledge that this environmental monitoring approach is unable to detect viruses—they require living cells to replicate, not nutrient media as for bacteria and fungi. Viruses are much smaller than bacterial spores, and although in theory should be captured by a HEPA filter, the process is absolutely blind to detect any should they migrate through the filtration system because of filter loading, filter leakage or just statistical probability. Both industry and the regulators are crucially aware of this environmental monitoring problem and it is only a matter of time before amendments to the cGMP will be adopted to address this Quality Assurance risk. The active filtration system addresses these four risk factors by eradicating all microbial organisms potentially present in the air generated by the HVAC system responsible for controlling the aseptic conditions of the manufacturing process.

The second important feature of the active filtration system related to the control of aseptic conditions is the ability to decompose VHP into its constituent components of water and oxygen in a single or multiple passes. This capability offers a significant reduction in time during the aeration phase of the VHP decontamination process with the benefit to the end user of increased uptime of the production isolator equipment. The aeration time required to get down to the human exposure limit of 1 ppm is four to five hours using the standard dilution approach. The primary reason for this is because the filter media itself retains VHP and slowly liberates itself over time. Since the active filtration system decomposes VHP, the retention problem associated with traditional HEPA is eliminated and valuable production efficiencies can be realized. It is also worth mentioning that there are new requirements for VHP decontamination levels to reach 10 ppb for new specialty drug products before production can begin. The time required to reach this level using the standard fresh air dilution method is eight to nine hours. The active VHP decomposition provided by the active filtration system will provide even greater benefit for these more stringent aseptic production applications.

The active filtration system provides an additional beneficial feature related to the control of aseptic conditions. A significant reduction in energy consumption can be realized because of the extremely low pressure drop the system provides. Standard HEPA filters provide a nominal pressure drop of 100 Pa when new and 200 Pa at replacement levels in aseptic production equipment. The pressure drop across the active filtration system is 10 Pa when new and 20 Pa if the industry uses the same two-times increase in $\Delta P$ across the filter as an indication of when to replace it. The 10 times reduction in pressure drop equates to a five to 10 times reduction in the energy needed to drive the HVAC fans responsible for maintaining air flow in the production equipment (equipment dependent). The active filtration system also has the potential to significantly increase air flow should it be desired for aeration or other purposes.

Example 2: Active Air Filtration for Composition Controlled Electronic Manufacturing Contamination from Volatile Organic Carbon (VOC) and Refractory Compounds (RC) are becoming increasingly important in controlled manufacturing environments. Both VOCs and RCs fit into the larger category of Airborne Molecular Contamination (AMC). In many respects, AMC is thought by many to be a greater threat to production yield than particulates in the microelectronic, data storage/hard disc drive and flat panel display production. This is because AMC is gas-phase contamination in trace levels that can interact adversely with critical surfaces. VOC and RC contamination result in unwanted chemical reactions. The product of these reactions is a film called Surface Molecular Contamination (SMC) that can change the chemical, electrical, physical and optical properties of these surfaces. AMC/SMC is proven to cause yield loss, premature product degradation and product failures in today's leading edge manufacturing processes. Examples of SMC related production issues are: Hazing of optical components used in lithography (RC), surface wettability (VOC), uneven oxide growth (VOC), decreased metal pad adhesion (VOC), stiction (VOC) and surface wet-ability (VOC).

ISO Technical Committee 209 created ISO 14644-8, Cleanrooms and associate controlled environments—Part 8: Classification of airborne molecular contamination—in 2006 to provide guidance to industry as they developed environmental monitoring strategies for this relatively new form of process contamination. This standard covers the classification of AMC in cleanrooms and associated controlled environments by providing airborne concentrations of specific chemical substances and a protocol for testing. Microelectronic, data storage and flat panel display producers use this standard in part to develop AMC monitoring and testing strategies and limits for their critical manufacturing processes. Although there are a number of mitigation approaches currently being used to address AMC related yield loss by these companies, activated carbon filtration systems are the most generally accepted approach to date. AMC filtration efficiency depends on several factors including the surface area of the filter, gas velocity, porosity and resin composition, with overall VOC filtration efficiency reaching approximately 90% on a practical basis. However, VOC filters can also become a source of VOC emission as they are and reach their absorptive capacity. Compare this to 99.9995% particulate removal efficiency for a U15 HEPA filter and the problem of VOC/RC contamination becomes more obvious. New thinking on the topic is converging on the approach that the best approach to an AMC mitigation strategy, and in the scope of this discussion specifically VOC and RC, is through active elimination of these contaminants altogether.

In certain embodiments, the active air filtration system provides two significant benefits in connection with control of the composition of high-tech electronic manufacturing environments. First, Increased particle removal efficiencies are possible with increased electrostatic filter media residence time (thicker filtration media) while still providing low pressure drop for increased energy efficiency. Second, the active air filter oxidizes AMC species (VOC and RC) forming less hazardous reaction products through electron bombardment and generation of reactive species (such as Ozone and hydroxyl radicals). Thus, the active filtration system is capable of increased filtration of both airborne particles and AMC species while reducing the amount of energy required to force gas through the filtration system.

REFERENCES

U.S. Pat. No. 7,449,053.
U.S. Pat. No. 8,211,374.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of treating a cleanroom enclosure, the method comprising the steps of:
providing said cleanroom enclosure; and
flowing gas from within said cleanroom enclosure through an active filtration system or flowing gas through said active filtration system into said cleanroom enclosure, wherein said active filtration system decomposes one or more of molecular contaminants, particulate contaminants and process gases present in said gas into reaction products and reduces the abundance of particles present in said gas.

2. The method of claim 1, wherein said enclosure comprises a cleanroom, an equipment front end module, a mini-environment, a contamination controlled manufacturing environment, a glove box, a restricted air barrier system, an isolator or a freeze dryer.

3. The method of claim 1, wherein said reaction products are less reactive than said molecular contaminants, particulate contaminants, or process gases or wherein said reaction products are inert.

4. The method of claim 1, further comprising a step of:
monitoring a flow rate of said gas into or out of said enclosure or monitoring a flow rate of said gas through said active filtration system; and
monitoring a particle concentration, a molecular contaminant concentration or both within said enclosure or within said active filtration system; or
monitoring a residence time of said gas within said enclosure or within said active filtration system.

5. The method of claim 1, wherein said active filtration system comprises a corona discharge.

6. The method of claim 1, wherein said active filtration system generates ozone within said active filtration system having concentration of less than 10 ppm.

7. The method of claim 1, wherein said active filtration system comprises an electrostatic filter.

8. The method of claim 1, wherein said active filtration system comprises a HEPA or ULPA filter for uptake of carbon containing reaction products generated by the air filtration system.

9. The method of claim 1 further comprising:
monitoring at least one first parameter of said enclosure or said active filtration system; and
adjusting at least one second parameter of said active filtration system in a controlled feedback loop based on said monitoring of said first parameter to control the decomposition of molecular contaminants, particulate contaminants, process gases or any combination thereof or to control the reduction of particles.

10. The method of claim 9, wherein said first parameter is selected from the group comprising: an ozone concentration, a concentration of molecular contaminants, a microbial contaminant concentration, a particulate concentration, an electrostatic charge, a pressure, a gas flow rate, a gas velocity, and a concentration of airborne molecular contamination (AMC); and
wherein said second parameter is selected from the group comprising: an ozone concentration, a pressure, an electrostatic charge, a gas flow rate and a gas velocity.

11. The method of claim 1, wherein said active filtration system exhibits a pressure drop less than or equal to 30 Pa.

12. The method of claim 1, wherein said enclosure is a contamination controlled enclosure for the production of electronic systems or optical systems and wherein said one or more molecular contaminants or process gases comprise volatile organic compounds, refractory compounds or both.

13. The method of claim 1, wherein said enclosure is for preparation, manufacture, storage, transfer, fill or finish of a sterile pharmaceutical or biological, a sterile pharmaceutical or biological container or a sterile pharmaceutical or biological delivery device.

14. The method of any of claim 1, wherein said enclosure is for preparation, manufacture, storage, transfer or processing of food or drink or wherein said enclosure is for preparation, manufacture, storage, transfer or processing of a cosmetic.

15. The method of any of claim 1, further comprising the step of sterilizing gas and surfaces within the enclosure by introducing a gas-phase sterilant into said enclosure for a sufficient time to effect sterilization of said gas and surfaces, wherein said active filtration system decomposes said gas-phase sterilant into said reaction products.

16. The method of claim 15, wherein sterilizing gas and surfaces within said enclosure by introducing said gas-phase sterilant into said enclosure occurs during a conditioning phase, a decontamination phase or an aeration phase.

17. The method of claim 15, wherein reducing a concentration of said gas-phase sterilant in said enclosure occurs by transporting said gas through said active filtration system and out of said enclosure or by transporting said gas through said active filtration system and returning treated gas to said enclosure.

18. The method of claim 15, wherein said active filtration system reduces the viability of biological particles in said gas.

19. The method of claim 15, further comprising the step of reducing a concentration of said gas-phase sterilant in said enclosure to below 1 ppm over a time period of less than 3 hours.

20. The method of claim 15, wherein said gas-phase sterilant comprises one or more of hydrogen peroxide, ethylene oxide, and formaldehyde.

21. The method of claim 15 further comprising reducing a humidity within said enclosure prior to said step of sterilizing gas and surfaces within said enclosure by introducing said gas-phase sterilant into said enclosure.

22. A method of reducing a concentration of one or more sterilant process gases contained within a cleanroom enclosure, the method comprising the steps of:

providing said cleanroom enclosure containing said one or more sterilant process gases; and flowing gas from within said cleanroom enclosure through an active filtration system, wherein said active filtration system decomposes said one or more sterilant process gases present in said gas to reaction products, inactivates biological particles present in said gas, and filters particles present in said gas.

23. A method for controlling the gas composition within a cleanroom enclosure for the manufacture of electronics or optical systems, the method comprising the steps of:

providing said enclosure for the manufacture of electronics or optical systems; and flowing gas from within said cleanroom enclosure through an active filtration system or flowing gas through an active filtration system into said cleanroom enclosure, wherein said active filtration system decomposes one or more volatile organic compounds or refractory compounds present in said gas to reaction products and filters particles present in said gas.

* * * * *